US00RE49223E

(19) United States
(12) Reissued Patent
Kim et al.

(10) Patent Number: US RE49,223 E
(45) Date of Reissued Patent: Sep. 27, 2022

(54) WATER-SOLUBLE FLUORESCENCE COMPOUND AND METHOD FOR PREPARING THE SAME

(71) Applicants: SNU R&DB FOUNDATION, Seoul (KR); GLOBAL FRONTIER CENTER FOR MULTISCALE ENERGY SYSTEMS, Seoul (KR)

(72) Inventors: Seong Keun Kim, Seoul (KR); Il Seung Yang, Gyeonggi-do (KR); Seon Jin Hwang, Seoul (KR); Jung Eun Lee, Incheon (KR); Jong Woo Lee, Seoul (KR); Jun Hee Kang, Seoul (KR); Eun Hak Lim, Seoul (KR)

(73) Assignees: SNU R&DB FOUNDATION;, Seoul (KR); GLOBAL FRONTIER CENTER FOR MULTISCALE ENERGY SYSTEMS, Seoul (KR)

(21) Appl. No.: 16/861,294

(22) Filed: Apr. 29, 2020

Related U.S. Patent Documents

Reissue of:
(64) Patent No.: 10,077,399
Issued: Sep. 18, 2018
Appl. No.: 15/384,241
Filed: Dec. 19, 2016

U.S. Applications:
(63) Continuation of application No. 14/344,574, filed as application No. PCT/KR2012/007137 on Sep. 5, 2012, now Pat. No. 9,708,237.

(30) Foreign Application Priority Data

Sep. 16, 2011 (KR) ..... 10-2011-0093191
Jul. 30, 2012 (KR) ..... 10-2012-0083376

(51) Int. Cl.

| | |
|---|---|
| ***C09K 11/06*** | (2006.01) |
| ***A61K 49/00*** | (2006.01) |
| ***A61N 5/06*** | (2006.01) |
| ***C07C 49/248*** | (2006.01) |
| ***C07C 49/255*** | (2006.01) |
| ***C07H 15/203*** | (2006.01) |
| ***H01L 51/00*** | (2006.01) |
| ***H01L 51/50*** | (2006.01) |

(52) U.S. Cl.
CPC ..... *C09K 11/06* (2013.01); *A61K 49/0021* (2013.01); *A61K 49/0052* (2013.01); *A61K 49/0054* (2013.01); *A61N 5/062* (2013.01); *C07C 49/248* (2013.01); *C07C 49/255* (2013.01); *C07H 15/203* (2013.01); *H01L 51/0052* (2013.01); *H01L 51/5012* (2013.01); *C09K 2211/1011* (2013.01)

(58) Field of Classification Search
CPC ..... C09K 11/06; C09K 2211/1011; C09K 19/3469; A61N 5/062; H01L 51/0052; H01L 51/5012; H01L 51/0062; A61K 49/0021; A61K 49/0052; A61K 49/0054; C07H 15/203; C07C 49/248; C07C 49/255
See application file for complete search history.

(56) References Cited

U.S. PATENT DOCUMENTS 5,847,225 A * 12/1998 Ramachandran ..... C07C 45/62 568/313
2002/0102309 A1* 8/2002 Hirsh ..... A61K 9/2059 424/490
2010/0081724 A1 4/2010 Souto

FOREIGN PATENT DOCUMENTS

KR 10-2009-0041632 4/2009
WO 2009/054608 4/2009
WO 2013/039308 A2 3/2013

OTHER PUBLICATIONS

Ilseung Yang, et al., "Photochemical Generation of a new, highly Fluorescent Compound from Non-Fluorescent Resveratrol", Chemical Communications, (Feb. 24, 2012), pp. 3839-3841, pp. 1-3.
Kim, et al., "A Two-Photon Fluorescent Probe for Lipid Raft Imaging: C-Laurdan", Wiley-VCH Verlag Gmbh & Co., KGaA, Weinheim, ChemBioChem (2007) vol. 8, pp. 553-559, pp. 1-7.
Kim, et al. "Two-Photon Fluorescent Turn-On Probe for Lipid Rafts in Live Cell and Tissue," Department of Chemistry, National Creative Research Initiative Center for Cell Dynamics, Department of Physics http://pubs.acs.org/journals/iacsat, JACS Communications (Mar. 11, 2008) pp. 1-2.
Kim, et al., "Photochemical Generation of a New, Highly Fluorescent Compound from Non-Fluorescent Resveratrol", Chemical Communications, (Feb. 24, 2012) pp. 1-3.
Lemhadri et al., "Palladium-Catalyzed Heck Reasctions of alk-1-en-3-ones with Aryl Bromides: A Very Simple Access to (E)-1-arylalk-1-en-3-one," (Nov. 18, 2008) pp. 1021-1035, pp. 15.
Rodriguez-Bernaldo de Quiros et al., "Analysis of Non-Anthocyanin Phenolic Compounds in Wine Samples Using High Performance Liquid Chromatography with Ultraviolet and Fluorescence Detection," Analytical Chemistry, Nutrition and Food Science, Department, J. Sep. Sci. (2007) pp. 1-5.

* cited by examiner

*Primary Examiner* — Jerry D Johnson
(74) *Attorney, Agent, or Firm* — Brundidge & Stanger, P.C.

(57) ABSTRACT

The present invention provides a water-soluble fluorescent compound of resveratrone 6-O-β-glucoside [(E)-4-(8-hydroxy-6-(((2S,3R,4S,5S,6R)-3,4,5-trihydroxy-6-(hydroxymethyl)tetrahydro-2H-pyran-2-yl)oxy)naphthalen-2-yl)but-3-en-2-one] and its derivatives of Formula I which have at least one water-soluble substituent, and a method for preparing the same by a photochemical reaction of resveratrol 3-O-β-glucoside and its derivatives of having Formula 3 which are not fluorescent.
Said new water-soluble fluorescent compounds has single-photon absorptive characteristics and/or two-photon absorptive characteristics as well as no or little toxicity, and can be usefully utilized in fields that requires water-soluble fluorescent characteristics (diagnosis, fluorescent probe, in vivo imaging, display, etc.).

7 Claims, 15 Drawing Sheets

WATER-SOLUBLE FLUORESCENCE COMPOUND AND METHOD FOR PREPARING THE SAME

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

The present application is a continuation of U.S. patent application Ser. No. 14/344,574, filed Oct. 7, 2014, incorporated herein by reference, which claims priority to 371 International application PCT/KR2012/007137, filed Sep. 5, 2012, which claims priority to KR 10-2012-0083376, filed Jul. 30, 2012; which claims priority to KR 10-2011-0093191, filed Sep. 16, 2011, which are incorporated herein by reference.

TECHNICAL FIELD

The present invention relates to a water-soluble fluorescent compound, a method for preparing the same, and its use.

BACKGROUND ART

There are cases where light is emitted from a substance at a low temperature at which the substance can not emit any visible ray by thermal radiation. Such lighting phenomenon is referred to as luminescence. Luminescence means the emission of light having a wavelength which correspond to the energy difference when a substance is converted to a stable state having low energy from an unstable state having high energy. Thus, in order to make a substance emit such light, it is necessary to make the substance to an unstable excited state having high energy. Various sources of energy such as light, chemical reactions, heat, electricity, cathode-emitted electron or the like may be used. Said difference sources of energy produce different types of light emission such as photo-, chemi-, thermo-, electro-, cathodo-luminecence, or the like.

Luminescence can be classified as fluorescence and phosphorescence. Fluorescence refers to the phenomenon that a substance emits light only when the substance is irradiated, and phosphorescence refers to the phenomenon that a substance continuously emits a light even after the irradiation to the substance is ended.

In this regard, a substance emitting fluorescence is referred to as a fluorescent element or a fluorescent substance. Such fluorescent substance can be divided into a single-photon absorption fluorescent substance which absorbs only one photon under a strong laser to emit the fluorescence and a multi-photon absorption fluorescent substance which absorbs a plurality of photons to emits the fluorescence. The present invention relates to a new water-soluble fluorescent compound simultaneously having a single-photon absorption fluorescent feature as well as a multi-photon absorption fluorescent feature, in particular, 2-photon absorption fluorescent feature.

In more particular, the present invention was completed by finding a new water-soluble fluorescent compound of (E)-4-(8-hydroxy-6-(((2S,3R,4S,5S,6R)-3,4,5-trihydroxy-6-(hydroxymethyl)tetrahydro-2H-pyran-2-yl)oxy)naphthalen-2-yl)but-3-en-2-one (hereinafter, referred to as resveratrone 6-O-β-glucoside or resveratrone glucoside) having a high single-photon absorptive efficiency and/or 2-photon absorptive efficiency after a photochemical reaction of a conventionally known glycosylated derivative of resveratrol, for example, polydatin (hereinafter, referred to as resveratrol 3-O-β-glucoside or resveratrol glucoside) which is frequently found in peanuts, grapes, berries and the like.

DISCLOSURE OF INVENTION

Technical Problem

The purpose of the present invention is to provide a new water-soluble fluorescent compound with high efficiency having single-photon absorptive characteristics and/or two-photon absorptive characteristics.

Also, the purpose of the present invention is to provide a method of preparing the above water-soluble fluorescent compound.

In addition, the purpose of the present invention is to provide the use of the water-soluble fluorescent compound having single-photon absorptive characteristics and/or two-photon absorptive characteristics.

Solution to Problem

In order to achieve the above purpose, the present invention provides a new water-soluble fluorescent compound as shown below and a method for preparing the same.

(1) A water-soluble fluorescent compound represented by the following formula 1:

[Formula 1]

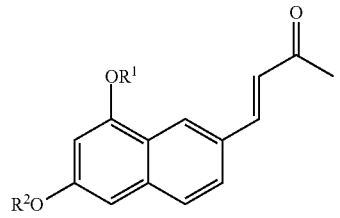

wherein, $R^1$ and $R^2$ are independently selected from the group consisting of hydrogen atom; straight-chain or branched $C_1$-$C_{10}$alkyl; $C_1$-$C_{10}$ alkylcarbonyl; $C_3$-$C_6$ cycloalkyl; $C_6$-$C_{30}$ aryl; and $C_5$-$C_{30}$ heteroaryl comprising at least one heteroatom N, O and/or S; a residue of a water-soluble natural compound such as glucosyl group; a residue of a water-soluble polymer such as polyethyleneglycol and polypropylene glycol; or a residue of a water-soluble high molecular organic compound, provided that at least one of $R^1$ and $R^2$ represents a residue of a water-soluble natural compound, a residue of a water-soluble polymer or a residue of a water-soluble high molecular organic compound.

(2) The water-soluble fluorescent compound represented by the following formula 2:

[Formula 2]

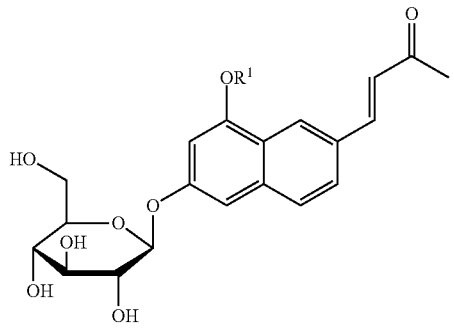

wherein, $R^1$ is the same as defined in claim 1.

(3) A method of preparing a water-soluble fluorescent compound represented by the following Formula 1, characterized in that it comprises a step of dissolving a compound represented by Formula 3 or its cis-isomer and mixture thereof in water or an organic solvent, and a step of subjecting to an UV irradiation:

[Formula 1]

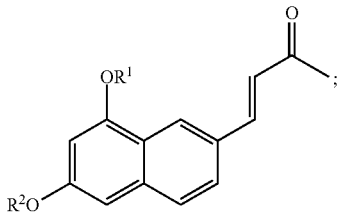

[Formula 3]

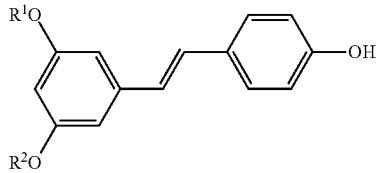

wherein, $R^1$ and $R^2$ are independently selected from the group consisting of hydrogen atom; straight-chain or branched $C_1$-$C_{10}$ alkyl; $C_1$-$C_{10}$ alkylcarbonyl; $C_3$-$C_6$ cycloalkyl; $C_6$-$C_{30}$ aryl; and $C_5$-$C_{30}$ heteroaryl comprising at least one heteroatom N, O and/or S; a residue of a water-soluble natural compound such as glucosyl group; a residue of a water-soluble polymer such as polyethylene glycol and polypropylene glycol; or a residue of a water-soluble high molecular organic compound, provided that at least one of $R^1$ and $R^2$ represents a residue of a water-soluble natural compound, a residue of a water-soluble polymer or a residue of a water-soluble high molecular organic compound.

(4) An organic fluorescent element comprising the water-soluble fluorescent compound of (1) above.

(5) A display element comprising the organic fluorescent element of (4) above.

(6) A spectrometer, a two-photon absorptive storing device, a laser micro processing apparatus, or a photo dynamic therapy apparatus, comprising the organic fluorescent element of (4) above.

Advantageous Effects of Invention

The water-soluble organic fluorescent compound according to the present invention can be prepared in high efficiency and high yield by a simple method.

The new water-soluble organic fluorescent compound of the present invention has excellent fluorescent characteristics single-photon absorptive characteristics and two-photon absorptive characteristics) as well as no or little toxicity according to a cytotoxity test, and thus can be used as a material of sunblock or fluorescent material by itself. In particular, it can be particularly used advantageously in fields requiring water-soluble fluorescent characteristics (diagnosis, fluorescent probe, in vivo imaging, display, etc.).

BEST MODE FOR CARRYING OUT THE INVENTION

Figure 1:
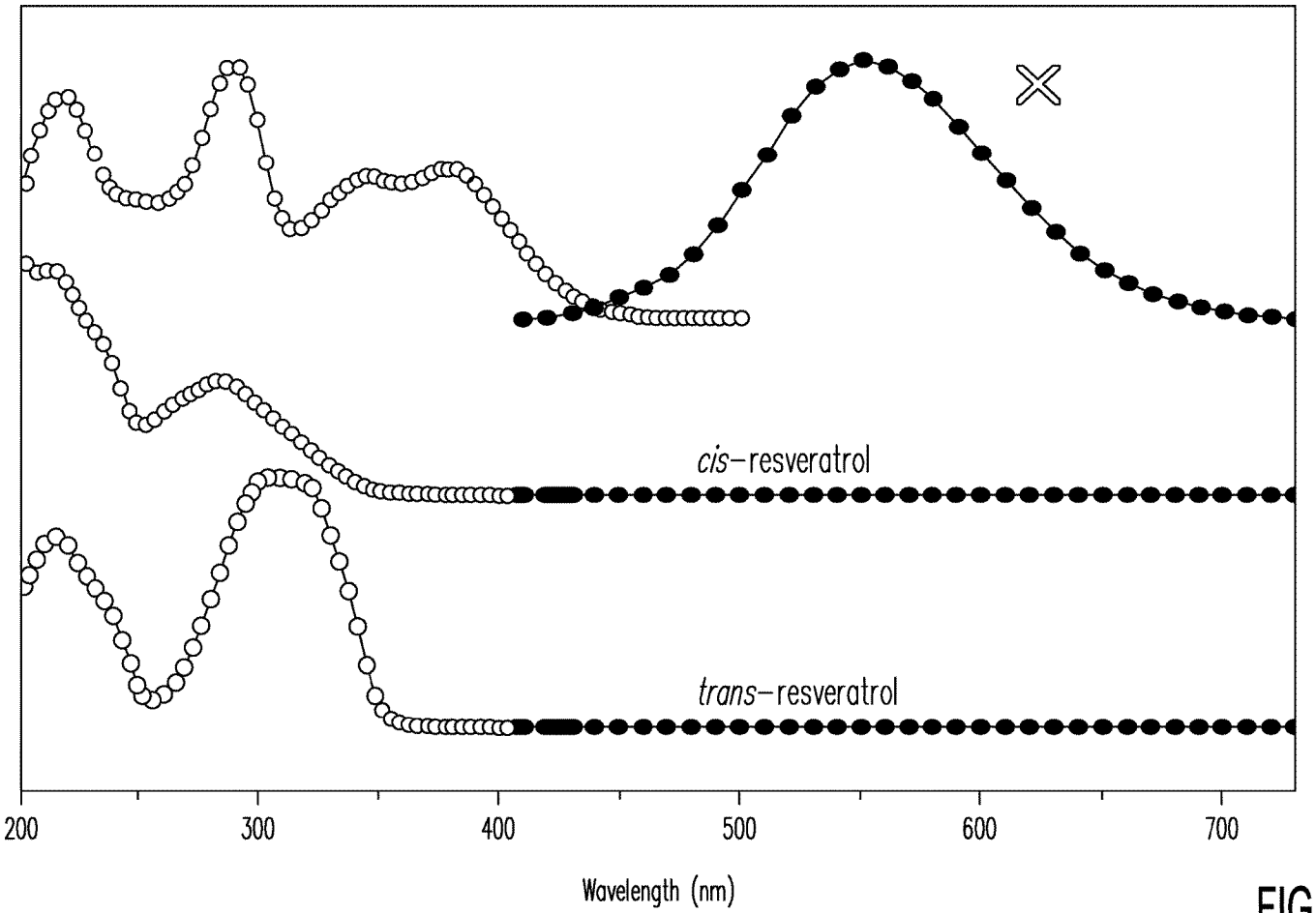
FIG. 1 is a graph showing emission spectra of non-fluorescent resveratrol and the fluorescent resveratron obtained in the Reference Example of the present invention (wherein the highly fluorescent species is denoted by X).

Hereinafter, the constitution and effect of the present will be explained in more detail.

The present invention provides a water-soluble fluorescent compound represented by the following formula 1:

[Formula 1]

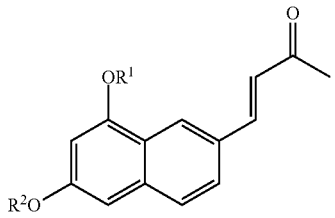

wherein, $R^1$ and $R^2$ are independently selected from the group consisting of hydrogen atom; straight-chain or branched $C_1$-$C_{10}$ alkyl; $C_1$-$C_{10}$ alkylcarbonyl; $C_3$-$C_6$ cycloalkyl; $C_6$-$C_{30}$ aryl; and $C_5$-$C_{30}$ heteroaryl comprising N, O and/or S as at least one heteroatom; a residue of a water-soluble natural compound such as glucosyl group; a residue of a water-soluble polymer such as polyethyleneglycol and polypropylene glycol; or a residue of a water-soluble high molecular organic compound, provided that at least one of $R^1$ and $R^2$ represents a residue of a water-soluble natural compound, a residue of a water-soluble polymer or a residue of a water-soluble high molecular organic compound.

In particular, the present invention provides a water-soluble fluorescent compound represented by the following formula 2:

[Formula 2]

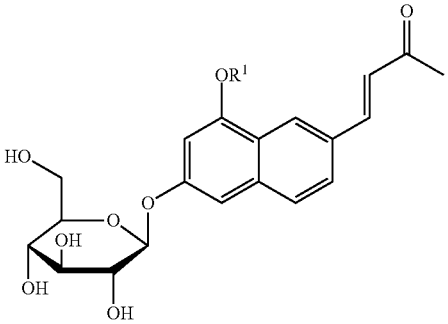

[wherein, $R^1$ is the same as defined in claim 1.]

Also, the present invention provides a method of preparing a water-soluble fluorescent compound represented by the above formula 1.

In particular, the present invention provides a method of preparing a water-soluble fluorescent compound represented by the following Formula 1, characterized in that it comprises a step of dissolving a compound represented by Formula 3 in water or an organic solvent, and a step of subjecting to an UV irradiation:

[Formula 1]

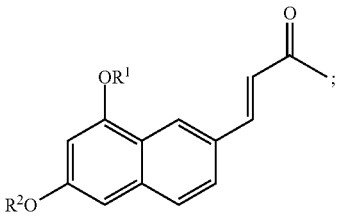

-continued

[Formula 3]

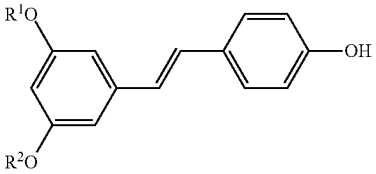

[wherein, $R^1$ and $R^2$ are independently selected from the group consisting of hydrogen atom; straight-chain or branched $C_1$-$C_{10}$ alkyl; $C_1$-$C_{10}$ alkylcarbonyl; $C_3$-$C_6$ cycloalkyl; $C_6$-$C_{30}$ aryl; and $C_5$-$C_{30}$ heteroaryl comprising at least one heteroatom N, O and/or S; a residue of a water-soluble natural compound such as glucosyl group; a residue of a water-soluble polymer such as polyethyleneglycol and polypropylene glycol; or a residue of a water-soluble high molecular organic compound, provided that at least one of $R^1$ and $R^2$ represents a residue of a water-soluble natural compound, a residue of a water-soluble polymer or a residue of a water-soluble high molecular organic compound.]

With regard to the present invention, at least one of $R^1$ and $R^2$ must be a water-soluble substituent selected from the group consisting of a residue of a water-soluble natural compound, a residue of a water-soluble polymer or a residue of a water-soluble high molecular organic compound. Examples of water-soluble natural compound that can be used as water-soluble substituent may include a monosaccharide, a disaccharide or oligomer thereof such as glucose, fructose, galactose, dextran, a water-soluble cellulose derivative or the like, an amino acid or oligomer thereof, a water-soluble vitamin, etc. As a water-soluble polymer or a water-soluble high molecular substance which can be used as a water-soluble substituent, various substances are known and a mention can be made, for example, polyethylene glycol, polypropylene glycol, polyvinyl alcohol (PVA), crospovidone (1-Ethenyl-2-Pyrrolidinone homopolymer), polyvinylpyrrolidone (PVP), PVP-PVA or the like. As a water-soluble organic high molecular compound that can be used as water-soluble substituent can be exemplified by polyol.

In the present invention, the water-soluble substituent is not limited to the substances as mentioned above, and further, it is possible to use any substances which are bonded to a resveratrol derivative before photoreaction or a resveratron derivative after photoreaction to make the entire compound water-soluble.

In particular, the present invention provides a method of preparing a water-soluble fluorescent compound represented by the following formula 2 characterized by comprising the step of dissolving polydatin derivative represented by the following formula 4 in water or an organic solvent and the step of subjecting to UV irradiation.

[Formula 2]

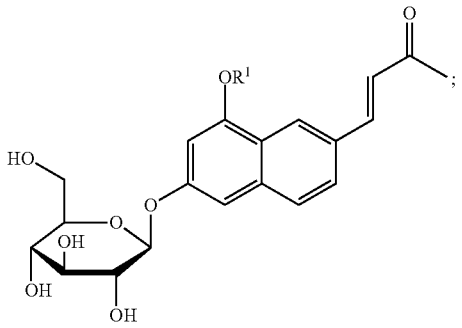

-continued

[Formula 4]

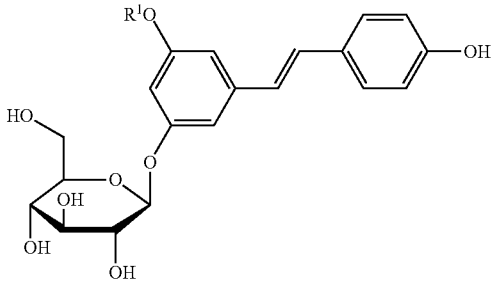

wherein, $R^1$ is the same as defined above.

According to one embodiment of the preparation method according to the present invention, the compound of formula 3 above can be used in the form of trans-isomer, cis-isomer or a mixture thereof.

In the glycosylated resveratrol of Formula 2 above, resveratrol. 3-O-beta-glucoside (hereinafter, referred to as polydatin) represented by the following formula 5 was first discovered from a medical plant of Polygonum cuspidatum Sieb, et Zucc, in 1960 s, and thereafter discovered in Sakhalin spruce, grapes, peanuts, and other plants. However, after 1970s, various pharmacological effect and efficiency are well known by pharmacological researches of the compound of formula 1, and thus many researches have been conducted.

Thus, according to a preferable embodiment of the present invention, a method of preparing a water-soluble fluorescent compound represented by the following formula 6 characterized by comprising the step of dissolving polydatin represented by the following formula 5 in water or an organic solvent and a step of subjecting to UV irradiation, is provided.

[Formula 5]

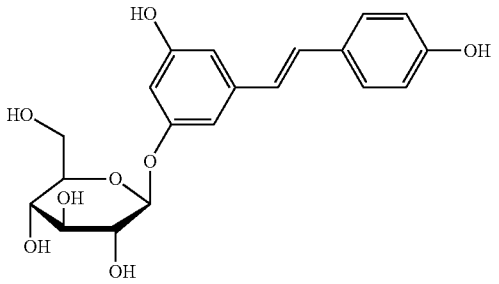

[Formula 6]

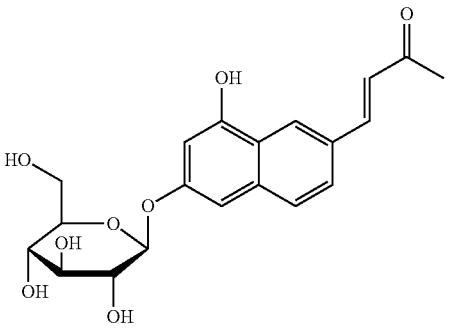

With regard to the present invention, since the glycosylated resveratrol derivatives of formula 3, in particular the polydatin of formula 5, is a substance existing in nature, it is known that it has no or little toxicity as well as its photochemical reaction products of formula 4 or formula 6 are expected to have no or little toxicity.

The priority application (Korean Patent Application No. 10-2011-0093191; filed on Sep. 16, 2011) of the present invention discloses a method for preparing (E)-4-(6,8-dihydroxynaphthalen-2-yl)bu-3-en-2-one (referred to as resveratrone) by photochemical reaction under UV ray from trans and/or cis-resveratrol according to reaction 1 below.

[Reaction Formula 1]

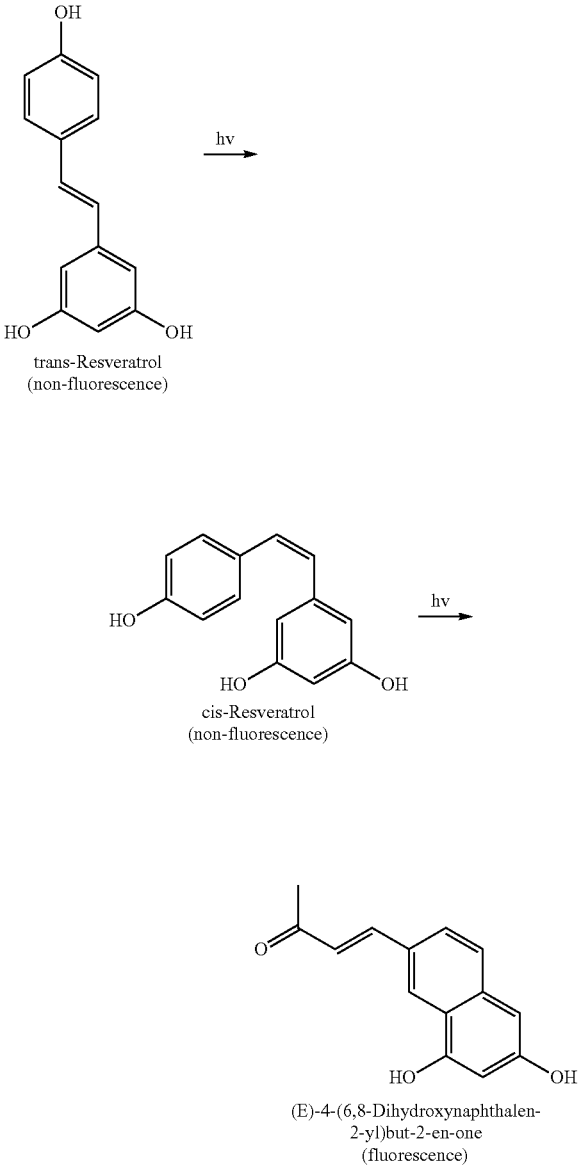

Also, the above Reaction formula 1 can be schematized as follows:

[Reaction formula 2]

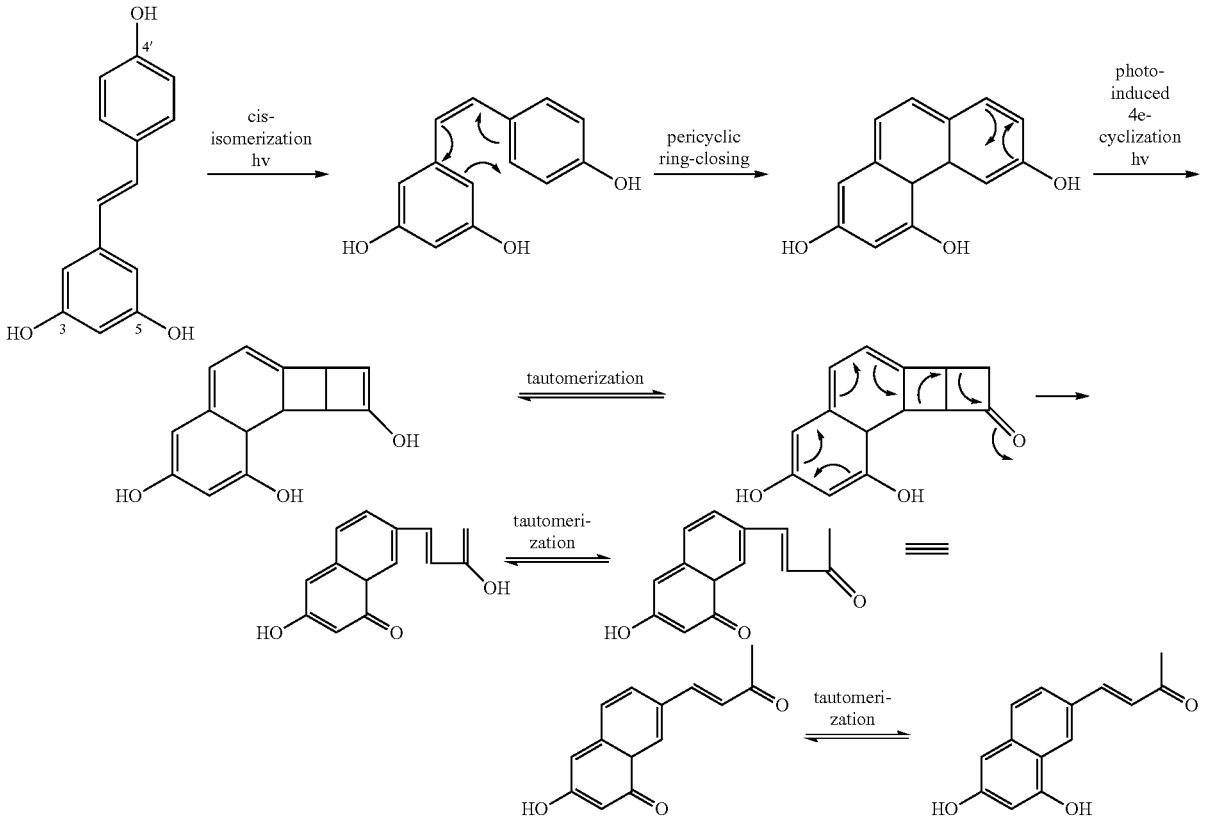

As to the organic solvent which can be used in the above Reaction Formula 1 and 2, it is possible to mention protic solvents such as ethanol, methanol, n-propanol, isopropanol, n-butanol, DMSO (dimethyl sulfoxide), EA (ethyl ester), THF (tetrahydrofuran) and the like, which can be used alone or as a mixture thereof. Ethanol, methanol, n-propanol, iso-propanol, n-butanol or DMSO are preferable, and DMSO is most preferable.

In some cases, in order to improve the yield of the product, the reaction mixture can additionally include an antioxidant such as, for example, ascorbic acid, polyphenol, glutathione, N-acetylcystein, alpha-tocopherol, butylated hydroxyanisole (BHA), catechin, quercetin, uric acid, bilirubin, glucose, flavonoid, or the like, which can be added alone or as mixture thereof, after dispersing or dissolving trans-resveratrol or cis-resveratrol in water or an organic solvent, and before subjecting to an UV irradiation. Among them, ascorbic acid or polyphenol is preferable.

Also, in some cases, in order to improve the yield of the product, it may be preferable to conduct the reaction under $N_2$ atmosphere or $N_2$ purging.

The reaction temperature at the photochemical reaction can be selected from −10~100° C., particularly 0 and 60° C., preferably between 10 and 40° C., and more preferably between 20 and 30° C. The wavelength of UV ray to be irradiated can be selected from 100~500 nm, preferably 200~400 nm, and more preferably 250~350 nm. The irradiation time can be selected from 5 sec~60 min, particularly 10 sec~40 min, preferably 15 sec~30 min, and more preferably 20 sec~25 min. In addition, the reaction temperature, UV wavelength and irradiation time is not strictly limited to the above ranges and can be easily modified according to the purpose.

Meanwhile, prior art (PCT/EP01/06103) discloses using polydatin of formula 5 above as sunblock. However, the present inventors confirmed that any photochemical reaction product could not be found even after irradiation of polydatin with natural light for a long period of time According to the present invention, the resveratrol moiety included in the non-florescent glycosylated resveratrol of Formula 3 above goes through a photochemical reaction under ultra violet rays and thus converts into a fluorescent glycosylated resveratrone of formula 1 via the a reaction so scheme substantially the same as Reaction Formulae 1 and 2 above. During the photochemical reaction, the glycoside part is maintained in the reaction product to allow the reaction product to be water-soluble.

Figure 2:
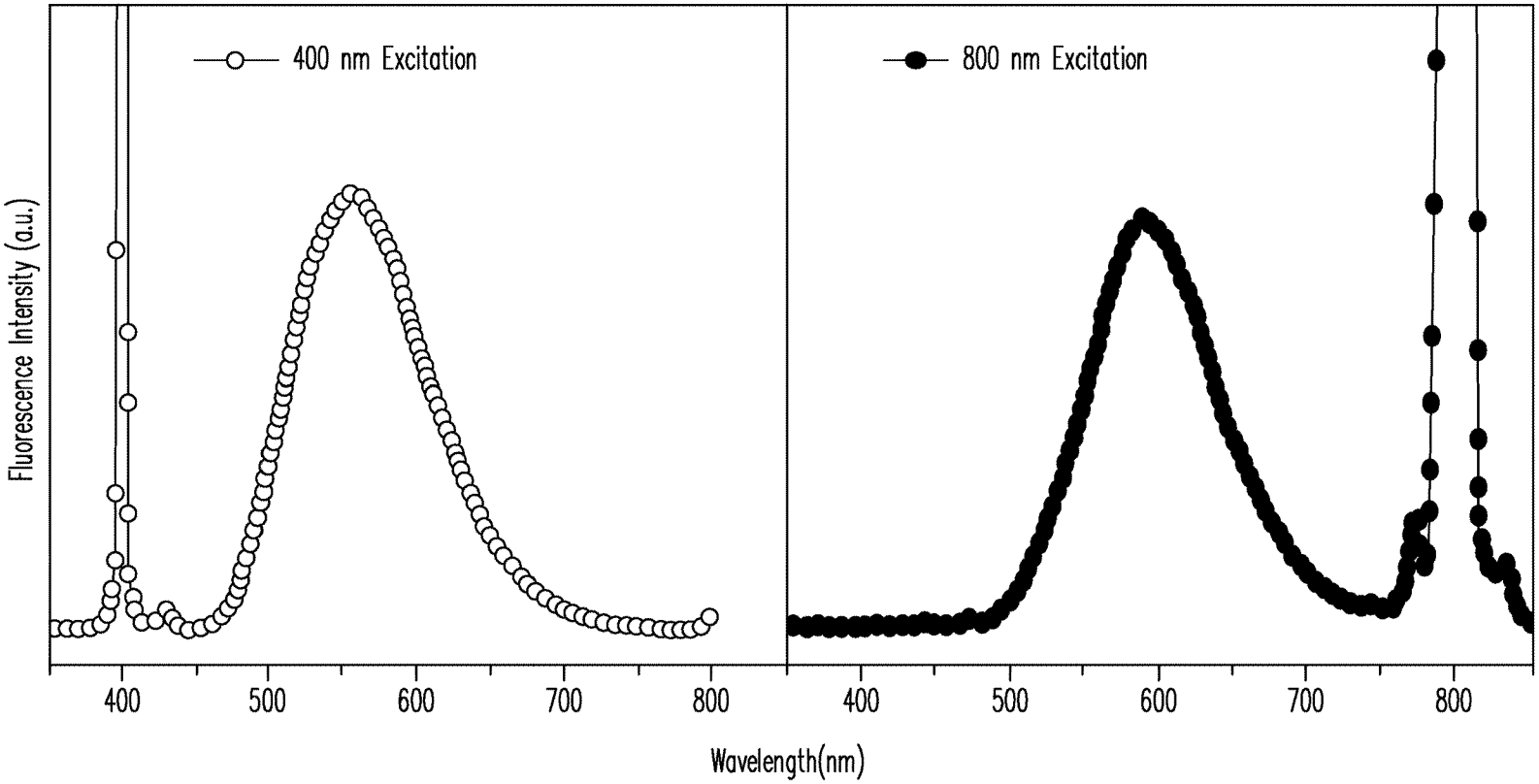
FIG. 2 is a graph showing a single-photon emission spectrum (left) and a two-photon emission spectrum (right) of the fluorescent resveratron.
Figure 3:
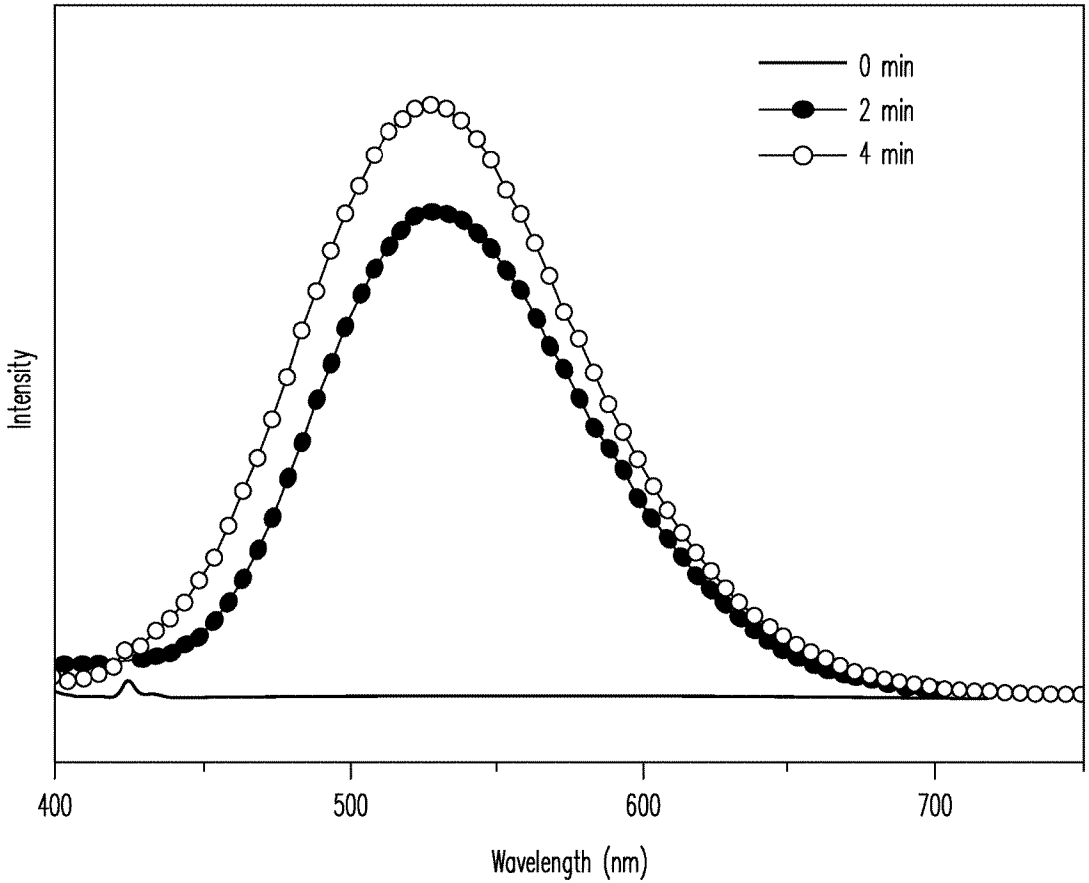
FIG. 3 is graph showing a change of single-photon emission spectra of the fluorescent resveratron.
Figure 4:
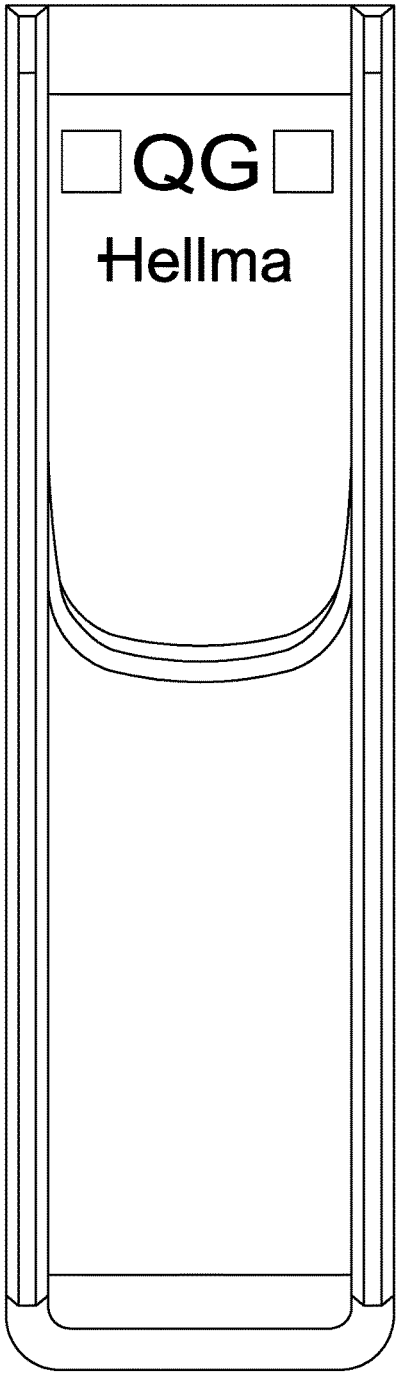
FIG. 4 is a photograph showing two-photon emission of the fluorescent resveratron.
Figure 5:
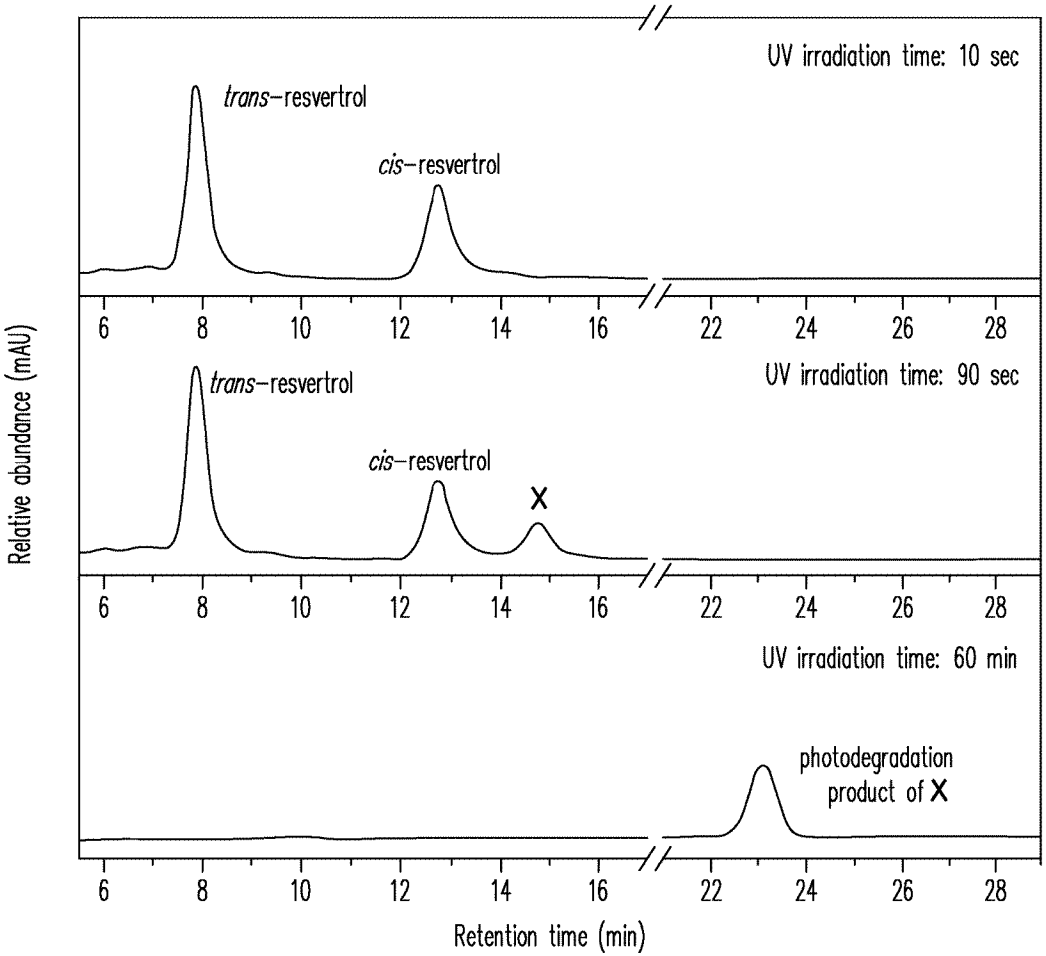
FIG. 5 is a HPLC graph for the reaction products obtained after different durations of exposure to UV irradiation (wherein the highly fluorescent species is denoted by X).

The fluorescent compound of the present invention prepared by the above method has high efficiency single-photon absorptive characteristics and/or two-photon absorptive characteristics (see FIGS. 2-4). Thus, the fluorescent compound of the present invention can be utilized in an organic fluorescent element including a fluorescent compound as well as in a display element including an organic fluorescent elements. The display element can be a plasma display panel, a cathode-ray tube (CRT), a lamp, or the like.

The water-soluble fluorescent compound obtained in the present invention is a new organic compound which has excellent fluorescent characteristics (i.e., single-photon absorptive characteristics and two-photon absorptive characteristics), is water-soluble, and has no or little toxicity.

Thus, the water-soluble fluorescent compound of the present invention can be utilized as sunblock or a raw material of fluorescent material by itself, and can be utilized in the field of cosmetics, imaging researches, organic fluorescent elements, display elements, spectrometers, two-photon absorptive storing devices, laser micro processing apparatus, photo dynamic therapy apparatus or the like.

In particular, the water-soluble fluorescent compound of the present invention is expected to be usefully utilized in the fields in which a water-soluble fluorescent substance with no or little toxicity is required, for example, in the field of cosmetics, diagnosis, fluorescent probe, a vivo imaging, display and the like.

Hereinafter, the present invention is explained in more detail with reference to the examples. However, the following examples are merely to exemplify the present invention and the present invention is not limited to the following examples and various corrections and modifications can be made.

MODE FOR THE INVENTION

In General $^{1}$H NMR and $^{13}$C NMR spectra are recorded on Bruker Avance 600 (Bruker Biospin, Germany) and Varian Inova-500 (Varian Assoc., Palo Alto, USA), wherein data are reported in the following order: chemical shift (δ) in ppm; multiplicities are indicated as bs (broadened singlet), s (singlet), d (doublet), m (multiplet), dd (doublet of doubled); coupling constants (J) are in Hertz (Hz).

Identification of the desired fluorescent compound is confirmed by high-resolution mass spectrometry (HRMS; LTQ orbitrab). HRMS analysis is conducted using a High-Resolution liquid Chromatography/Tandem Mass Analysis equipment located at the National Instrumentation Center for Environmental Management of Seoul National University.

UV absorption of the final fluorescent compound is determined by using a UV-VISIBLE spectrophotometer (Perkin Elmer, USA). Maximum values of excitation and emission are determined by using a fluorescent spectrophotometer (PTI, USA).

The absolute quantum yield is determined by using an absolute PL quantum yield measurement system (QE-1000, Otsuka Electronics, Japan). The relative quantum yield is determined by measuring the absorbance and emission intensity for each five concentrations for one solvent, determining the slope of said measured values, and comparing the slope with that of rhodamin 6G (the quantum yield of rhodamin 6G in ethanol is 0.95).

trans-Resveratrol and trans-pterostilbene are commercially available (from sigma-Aldlich and TCI, respectively). Other solvents and organic samples are purchased in the market and used without any additional purification unless there is any other description. Distilled water is completed by ion exchange and filtration.

Preparation of the Fluorescent Compound of the Present Invention

Reference Example 1

Preparation of (E)-4-(6,8-dihydroxynaphthalen-2-yl) but-3-en-2-one

A solution of trans-resveratrone (R5010, sigma-Aldlich; 125 μM) in 300 mL of methanol is subjected to a UV irradiation at 295 K for 90 seconds by using a UV lamp (λmax=305 nm) of 6-watt to give the titled compound of the following Formula 7.

[Formula 7]

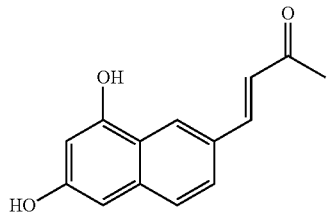

$^{1}$H NMR (600 MHz, MeOD) δ: 8.21 (s, 1H), 7.69 (d, J=16.2 Hz, 1H), 7.56 (dd, J=8.7, 1.1 Hz, 1H), 7.50 (d, J=8.7 Hz, 1H), 6.71 (d, J=16.2 Hz, 1H), 6.63 (d, J=1.7 Hz, 1H), 6.50 (d, J=1.9 Hz, 1H), 2.35 (s, 3H); $^{13}$C NMR (125 MHz, MeOD) 201.6, 159.1, 156.9, 147.1. 138.6, 128.9, 127.8, 127.1, 125.5, 125.1, 121.2, 102.1, 27.1; HRMS (ESI): m/z calcd for $C_{14}H_{11}O_3$ $[M]^-$ 227.0714, found 227.0742.

EXAMPLES 2-6

Except for conducting the photochemical reaction in the presence of an organic solvent such as ethanol (Reference Example 2), n-propanol (Reference Example 3), iso-propanol (Reference Example 4), n- butanol (Reference Example 5) or DMSO (Reference Example 6), respectively, the fluorescent compound is obtained from trans-resveratrol in the same manner as Reference Example 1. Quantum yields of each organic solvent are shown in Table 1.

TABLE 1

| | Solvent | Excitation (nm) | Emission (nm) | Relative quantum yield | Absolute quantum yield |
|---|---|---|---|---|---|
| Reference Example 1 | Methanol | 390 | 547 | 0.035 | 0.058 |
| Reference Example 2 | Ethanol | 390 | 540 | 0.103 | 0.145 |
| Reference Example 3 | n-Propanol | 390 | 534 | 0.155 | 0.212 |
| Reference Example 4 | iso-Propanol | 390 | 525 | 0.247 | 0.311 |
| Reference Example 5 | n-Butanol | 390 | 536 | 0.200 | 0.254 |
| Reference Example 6 | DMSO | 390 | 497 | 0.523 | 0.439 |

Reference Example 7

Except for using trans-pterostilbene as the reactant compound, the fluorescent compound is obtained from trans-resveratrol in the same manner as Reference Example 1.

The emission spectra of the obtained compound is shown in FIG. 3, wherein the time of 0 min, 2 min and 4 min means the UV irradiation, thus the spectrum at 0 min is for the reactant (trans-pterostilbene). As can be seen in FIG. 3, it can be confirmed that the final compound prepared from a non-fluorescent compound of trans-pterostilbene is a fluorescent compound.

Reference Example 8

Except for additionally adding ascorbic acid (50 μM, 40 μL) to a solution (125 μM) of trans-resveratrone (R5010, sigma-Aldlich; 8.559 mg) in 300 mL of methanol before subjecting to an UV irradiation, the fluorescent compound is obtained from trans-resveratrol in the same manner as Reference Example 1.

Figure 6:
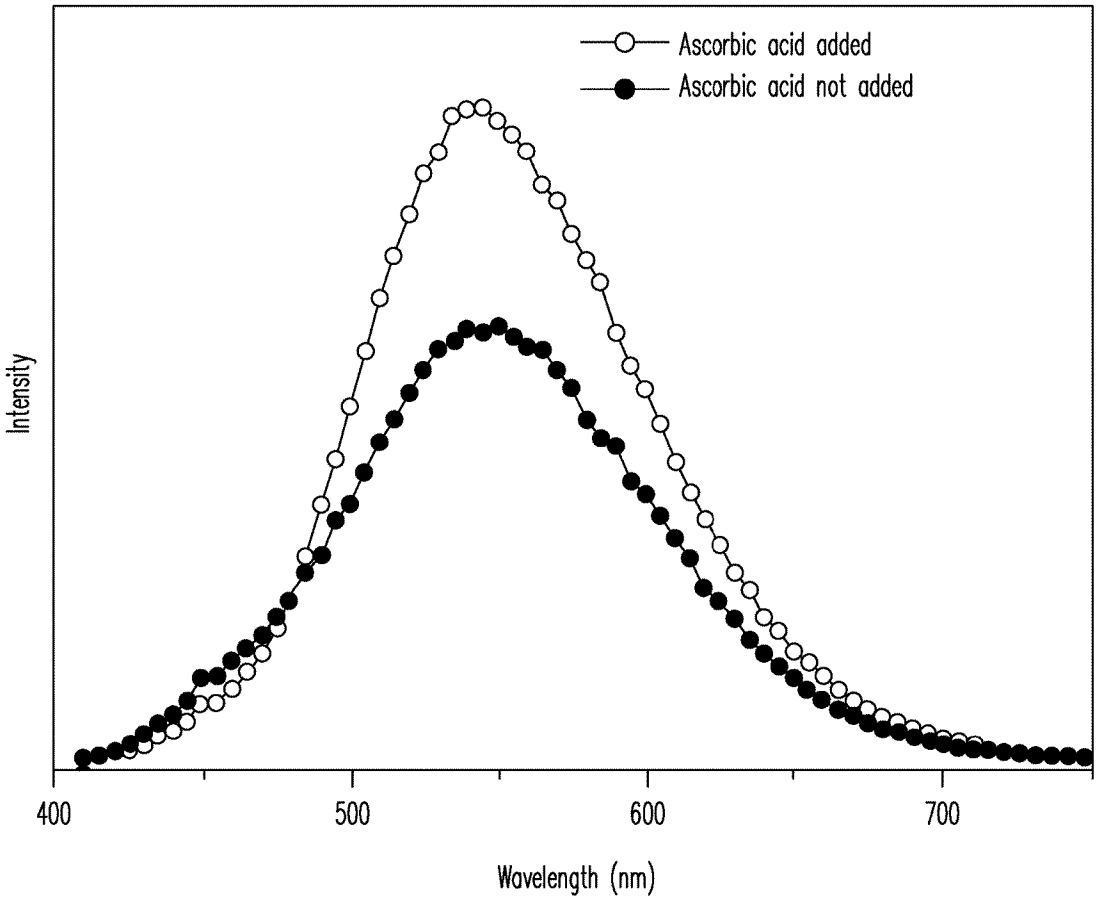
FIG. 6 is a graph showing the comparison of the intensity versus wavelength of the fluorescent resveratron which have been produced in the presence of ascorbic acid and in the absence of ascorbic acid, respectively.

FIG. 6 shows each graph of intensity versus wavelength of the final product obtained with adding ascorbic acid and the final product obtained without adding ascorbic acid. As can be seen in FIG. 6, it can be understood that the intensity of the final product obtained with adding ascorbic acid is higher than that obtained without adding ascorbic acid.

Reference Example 9

Except for conducting the photochemical reaction under $N_2$ atmosphere or with $N_2$ purging, the fluorescent compound is obtained frosts trans-resveratrol in the same manner as Reference Example 1.

Figure 7:
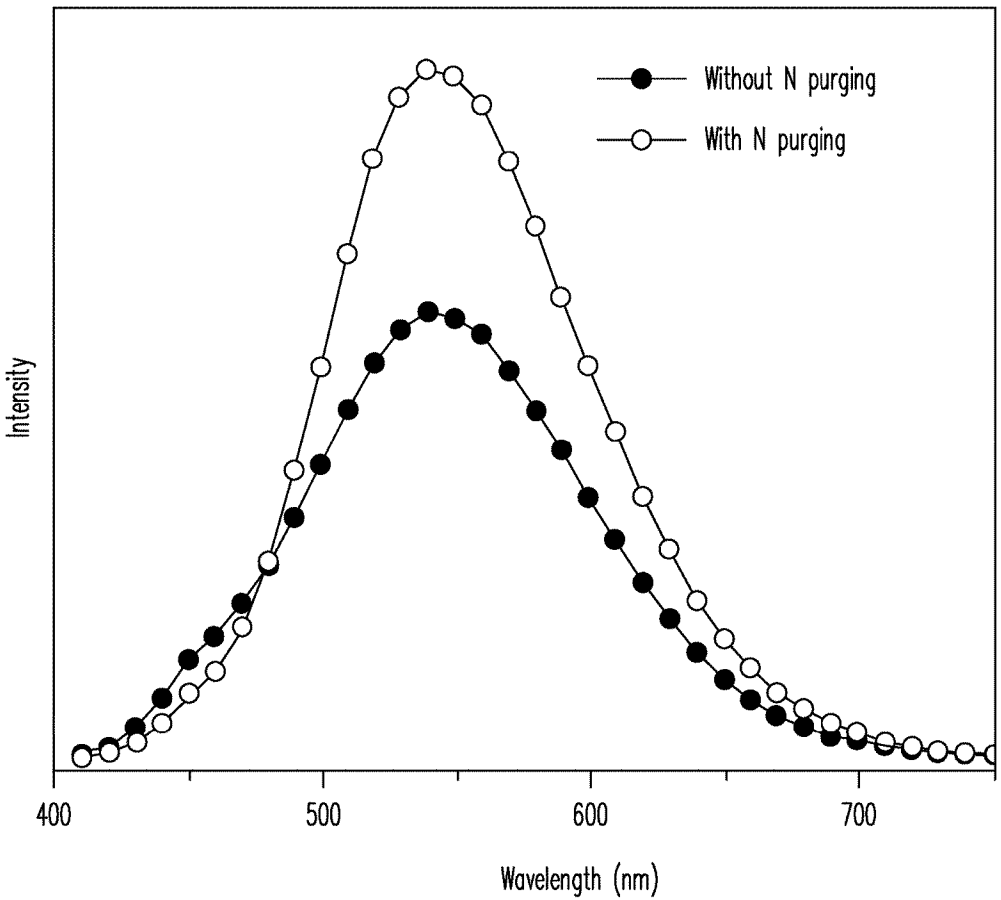
FIG. 7 is a graph showing the comparison of the intensity versus wavelength of the fluorescent resveratron which have been produced under $N_2$ atmosphere ($N_2$ purging) and not, respectively.

FIG. 7 shows each graph of intensity versus wavelength of the final product obtained with conducting under $N_2$ atmosphere and the final product obtained without conducting under $N_2$ atmosphere. As can be seen in FIG. 7, it can be understood that the intensity of the final product obtained with conducting under $N_2$ atmosphere is higher than that obtained without conducting under $N_2$ atmosphere.

Reference Example 10

Preparation of (Z)-4-(6,8-dihydroxynaphthalen-2-yl)-4-hydroxybut-3-en-2-one

Figure 8:
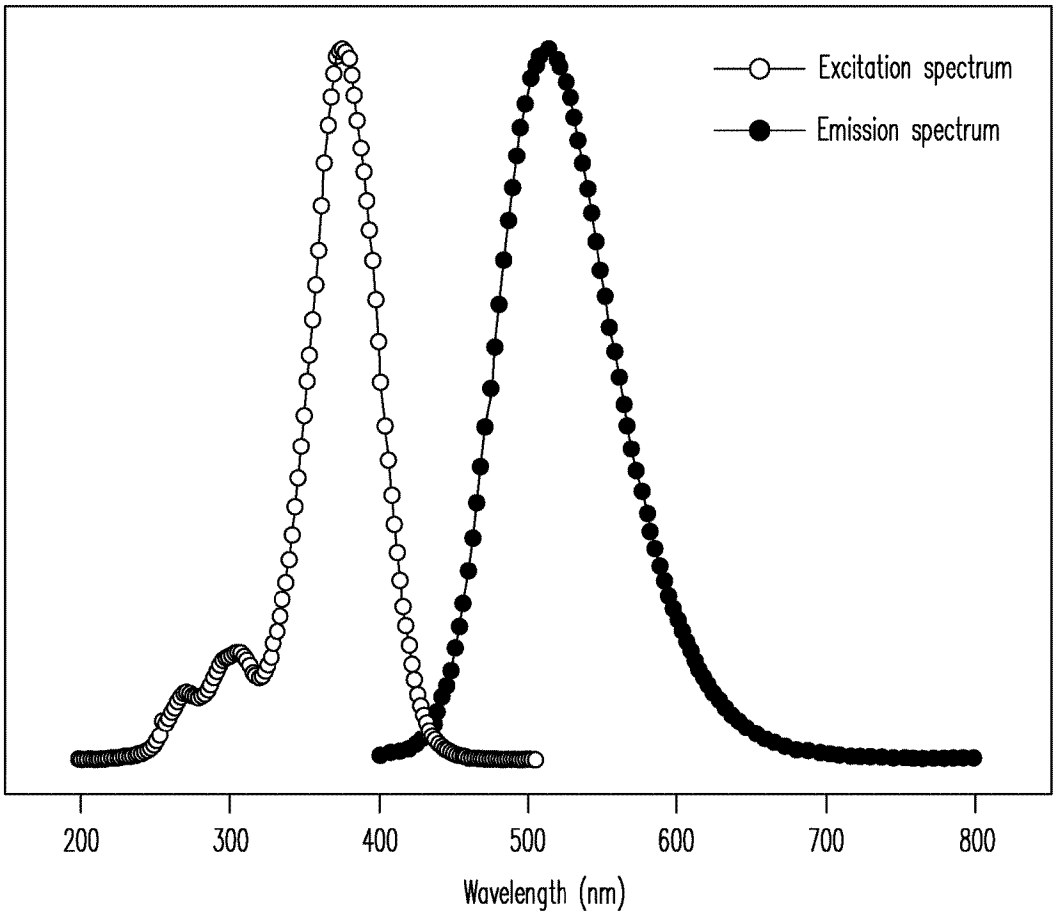
FIG. 8 is a graph showing an excitation spectrum of the reactant compound and an emission spectrum of the fluorescent compound obtained in Reference Example 10.

A solution of oxyresveratrol (9.159 mg) [O0373, SejinCI Company; 2,3',4,5'-Tetrahydroxy-trans-stilbene] in 300 mL of methanol is subjected to a UV irradiation at 295 K for 2 minutes by using a UV lamp (δmax=305 nm) of 6-watt to give the titled compound represented by following Formula 9. The excitation spectrum of the reactant compound and the emission spectrum of the final fluorescent compound are shown in FIG. 8.

[Formula 9]

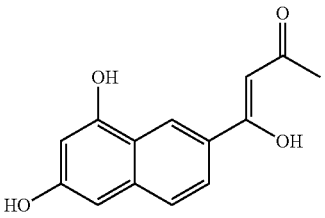

(Z)-4-(6,8-dihydroxynaphthalen-2-yl)-4-hydroxybut-3-en-2-one

Reference Example 11

Preparation of (E)-4-(5,7-dimethoxynaphthalen-3-yl)but-3-en-2-one

Figure 9:
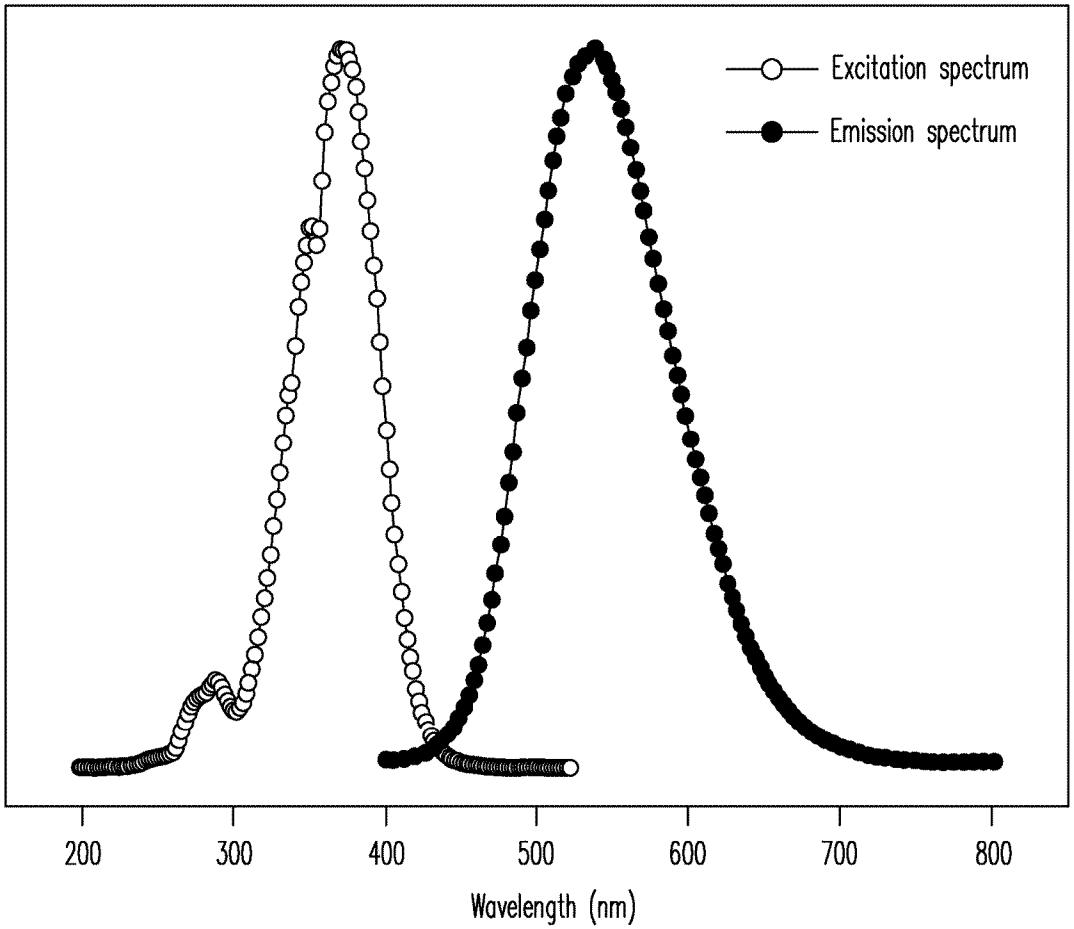
FIG. 9 is a graph showing an excitation spectrum of the reactant compound and an emission spectrum of the fluorescent compound obtained in Reference Example 11.

A solution of pterostilbene (9.611 mg) [P1928, SejinCI Company; trans-1-(3,5-Dimethoxyphenyl)-2-(4-hydroxyphenyl)ethylene] in 300 mL of methanol is subjected to a UV irradiation at 295 K for 5 minutes 30 seconds by using a UV lamp (λmax=305 nm) of 6-watt to give the titled compound represented by following Formula 10. The excitation spectrum of the reactant compound and the emission spectrum of the final fluorescent compound are shown in FIG. 9.

[Formula 10]

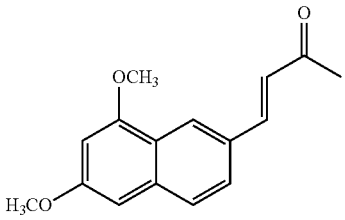

Reference Example 12

Preparation of (E)-4-(6,8-dihydroxynaphthalen-2-yl)methoxybut-3-en-2-one

Figure 10:
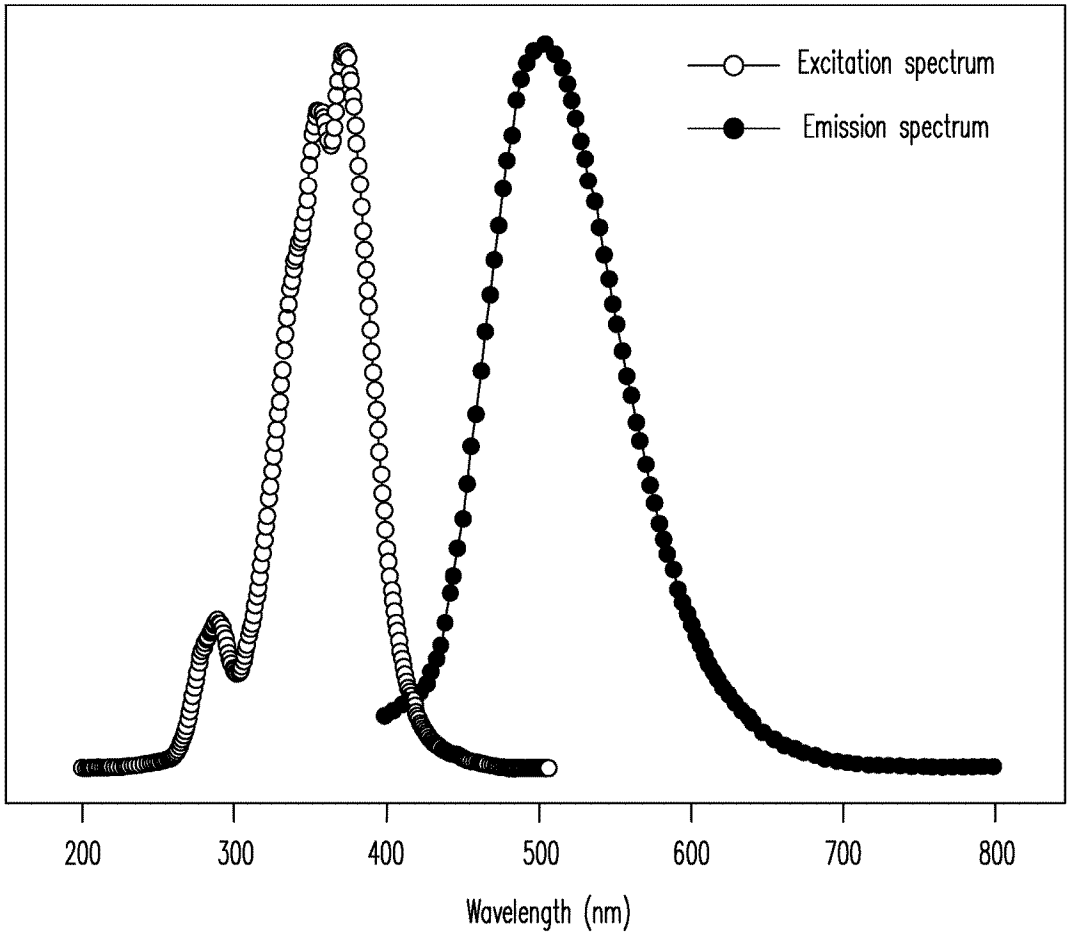
FIG. 10 is a graph showing an excitation spectrum of the reactant compound and an emission spectrum of the fluorescent compound obtained in Reference Example 12.

A solution of isorhapontigenin (9.685 mg) [I0804, SejinCI Company; 3,4',5-Trihydroxy-3'-methoxy-trans-stilbene] in 300 mL of methanol is subjected to a UV irradiation at 295 K for 7 minutes by using a UV lamp (λmax=305 nm) of 6-watt to give the titled compound represented by following Formula 11. The excitation spectrum of the reactant compound and the emission spectrum of the final fluorescent compound are shown in FIG. 10.

[Formula 11]

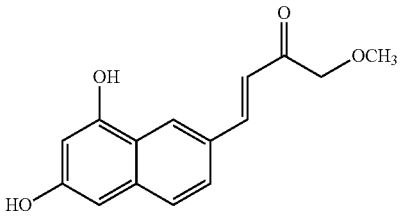

Reference Example 13

Preparation of (E)-4-(8-hydroxy-6-methoxynaphthalen-2-yl)but-3-en-2-one

Figure 11:
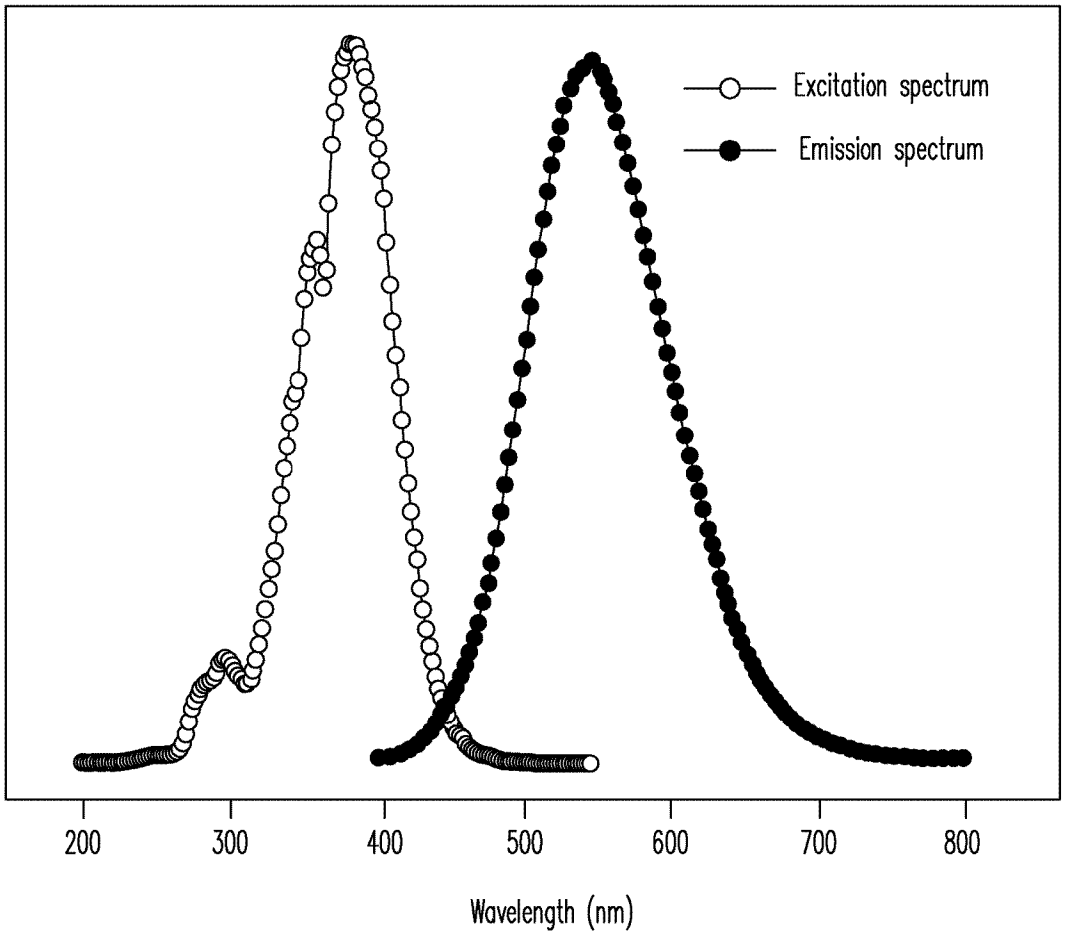
FIG. 11 is a graph showing an excitation spectrum of the reactant compound and an emission spectrum of the fluorescent compound obtained in Reference Example 13.

A solution of pinostilbene hydrate (9.085 mg) (SML0098, sigma-Aldlich; 3,4'-Dihydroxy-5-methoxy-trans-stilbene) in 300 mL of methanol is subjected to a UV irradiation at 295 K for 4 minutes 30 seconds by using a UV lamp (λmax=305 nm) of 6-watt to give the titled compound represented by following Formula 12. The excitation spectrum of the reactant compound and the emission spectrum of the final fluorescent compound are shown in FIG. 11.

[Formula 12]

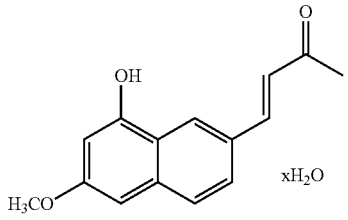

Example 1

Figure 12:
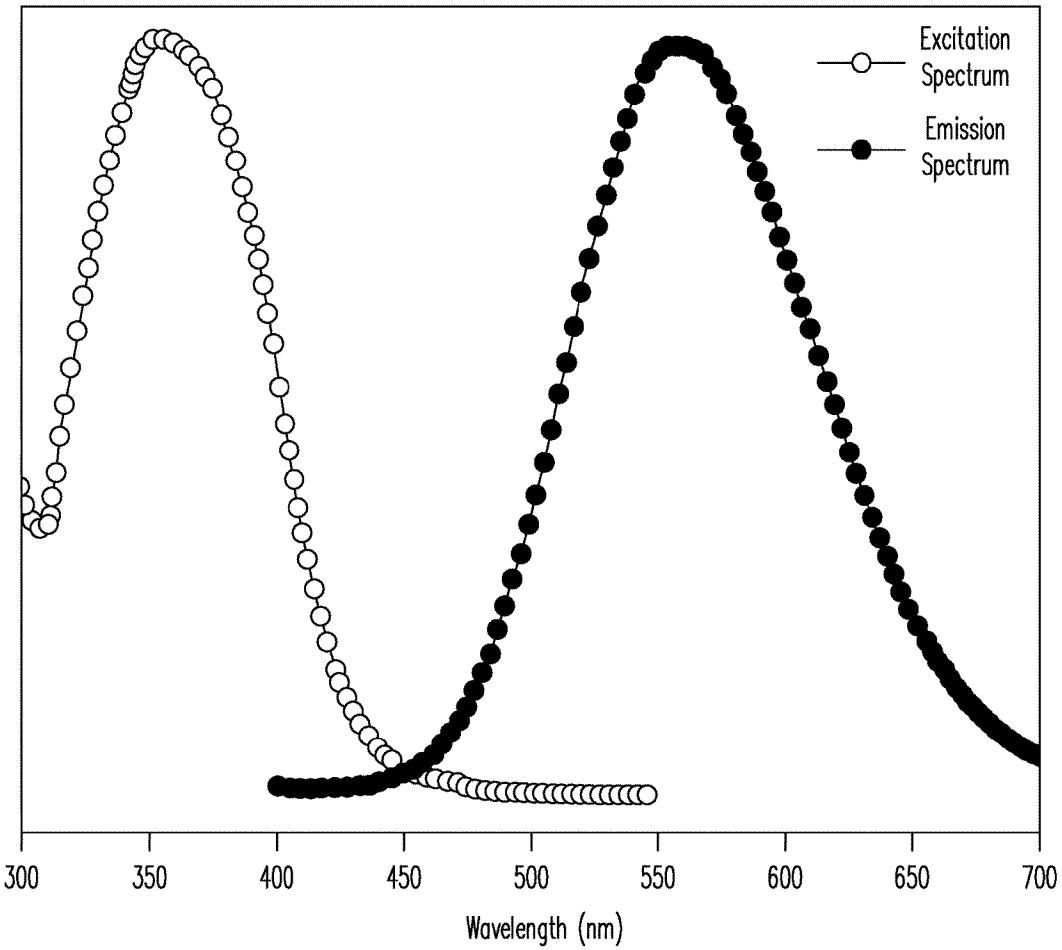
FIG. 12 is a graph showing an excitation spectrum of the reactant compound and an emission spectrum of the fluorescent compound (Resveratrone glycoside) obtained in Example 1.

Preparation of (E)-4-(8-hydroxy-6-(((2S,3R,4S,5S,6R)-3,4,5-trihydroxy-6-(hydroxymethyl)tetrahydro-2H-pyran-2-yl)oxy)naphthalen-2-yl)but-3-en-2-one A solution of polydatin (14.64 mg) (15721, sigma-Aldlich) in 300 mL of methanol is subjected to a UV irradiation at 295 K for 20 minutes by using a UV lamp (λmax=305 nm) of 6-watt to give the titled compound represented by following Formula 6. The excitation spectrum of the reactant compound and the emission spectrum of the final fluorescent compound are shown in FIG. 12.

[Formula 6]

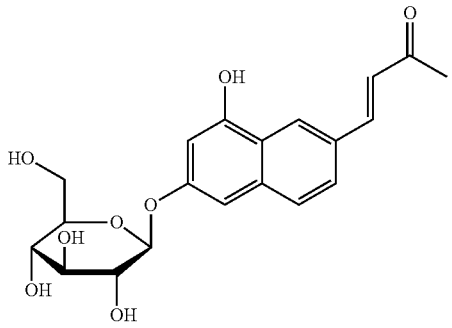

Example 2

A resveratrol derivative of the following formula haying a polyethyleneglycol succinate residue as a water-soluble substituent is prepared and subjected to a UV irradiation to give a water soluble fluorescent compound.

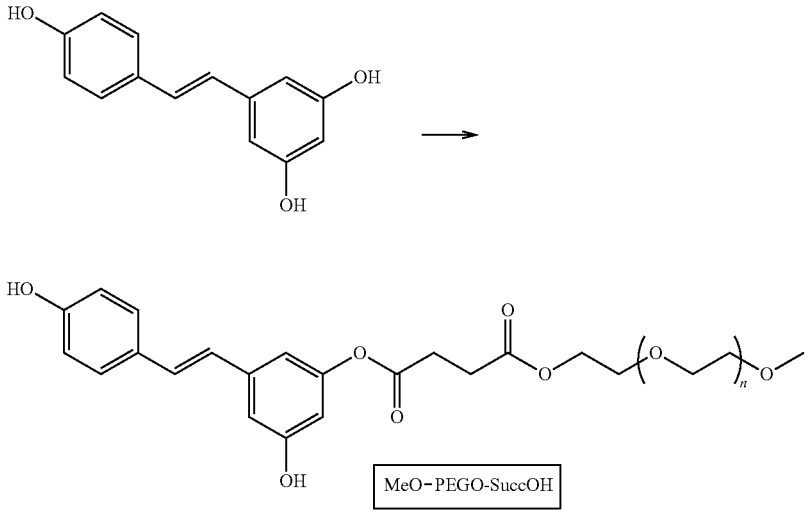

Example 3

A resveratrol derivative of the following formula having an oligoether dendrimer residue as a water-soluble substituent is prepared and subjected to a UV irradiation to give a water soluble fluorescent compound.

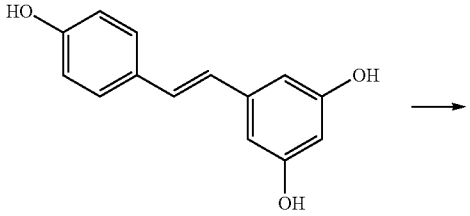

-continued

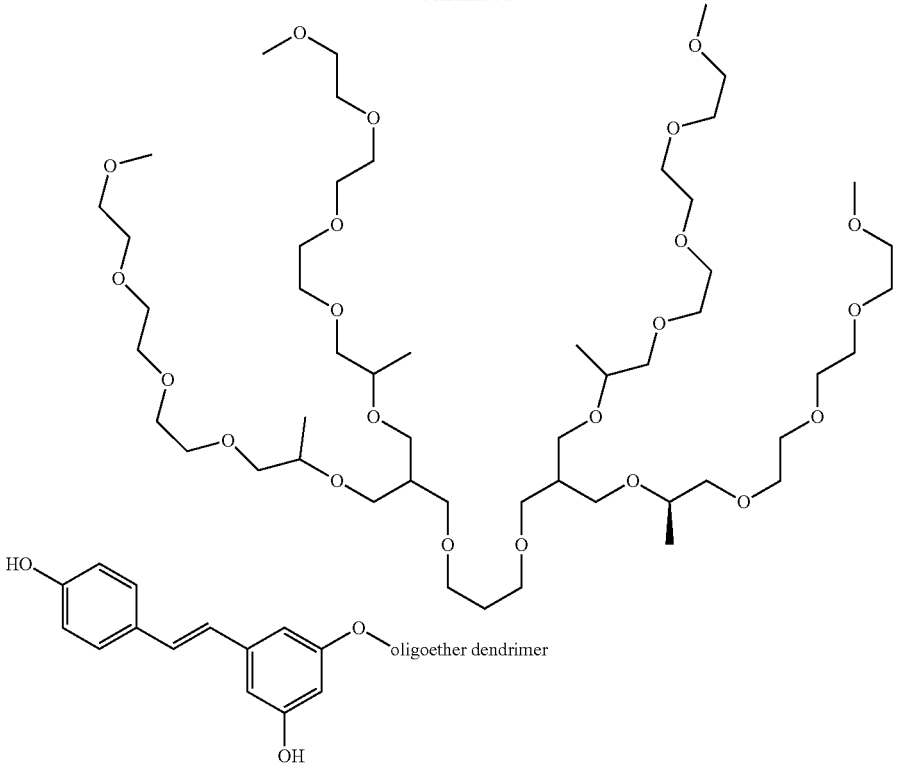

Test Examples

Cytotoxicity Test

In the presence of a test compound or a comparative compound, a cell line is cultured for a certain period of time (about 72 hours) and then a cytotoxicity test is conducted. As a control group, a blank test is conducted in the same manner as above without adding any compound including the test compound and the comparative compound.

Test Example 1

Cytomorphology Test

A breast epithelial cell line cultured in the presence of a test compound (Resveratrone glucoside, the water-soluble fluorescent compound obtained in Example 1) and a comparative compound (Etoposide, a commercial anticancer agent), respectively, and a microscopic examination is conducted to evaluate the cytomorphology and number change of the cultured cell.

Figure 13:
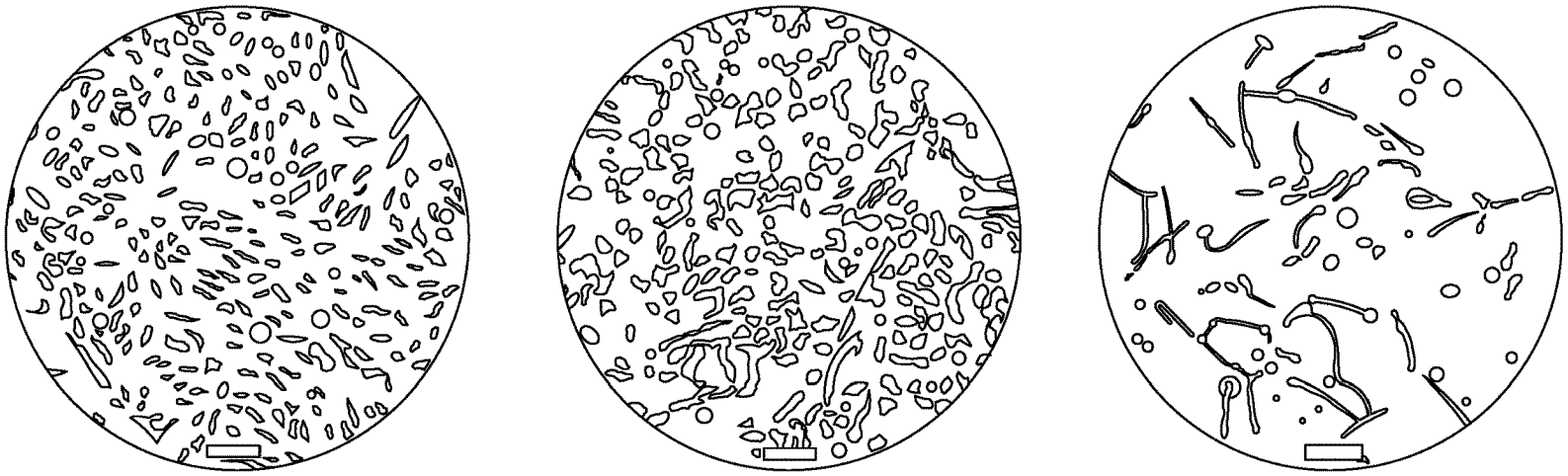
FIG. 13 is the photo images showing the result of Cytomorphology Test for a blank test (Control), a fluorescent compound of the present invention (Resveratrone glycoside) and a comparative compound (a commercial anticancer agent, Etoposide).

FIG. 13 shows each microscopic photo image of the resulting breast epithelial cells after cultured in a blank test (control group, left) and in the presence of the test fluorescent compound (Resveratrone glucoside, center) or the comparative compound(Etoposide, right), respectively. In FIG. 13, it can be confirmed that the comparative compound (Etoposide) results to a remarkable reduction in the number of cells in comparison with the control group, while the test compound (Resveratrone glucoside) has no significant difference from the control group.

Therefore, it can be understood from FIG. 13 that the test compound (Resveratrone glucoside) of the present invention has no or little cell toxicity and very high stability in comparison with the commercial anticancer agent (Etoposide).

Test Example 2

Trypan Blue Exclusion Test

To the each resulting breast epithelial cell cultured and microscopically examined in Test Example 1, a trypan blue test solution which does not dye cells alive is added and the number of cells alive is counted to evaluate the cell toxicity of the test compound and the comparative compound by comparing with the control group.

Figure 14:
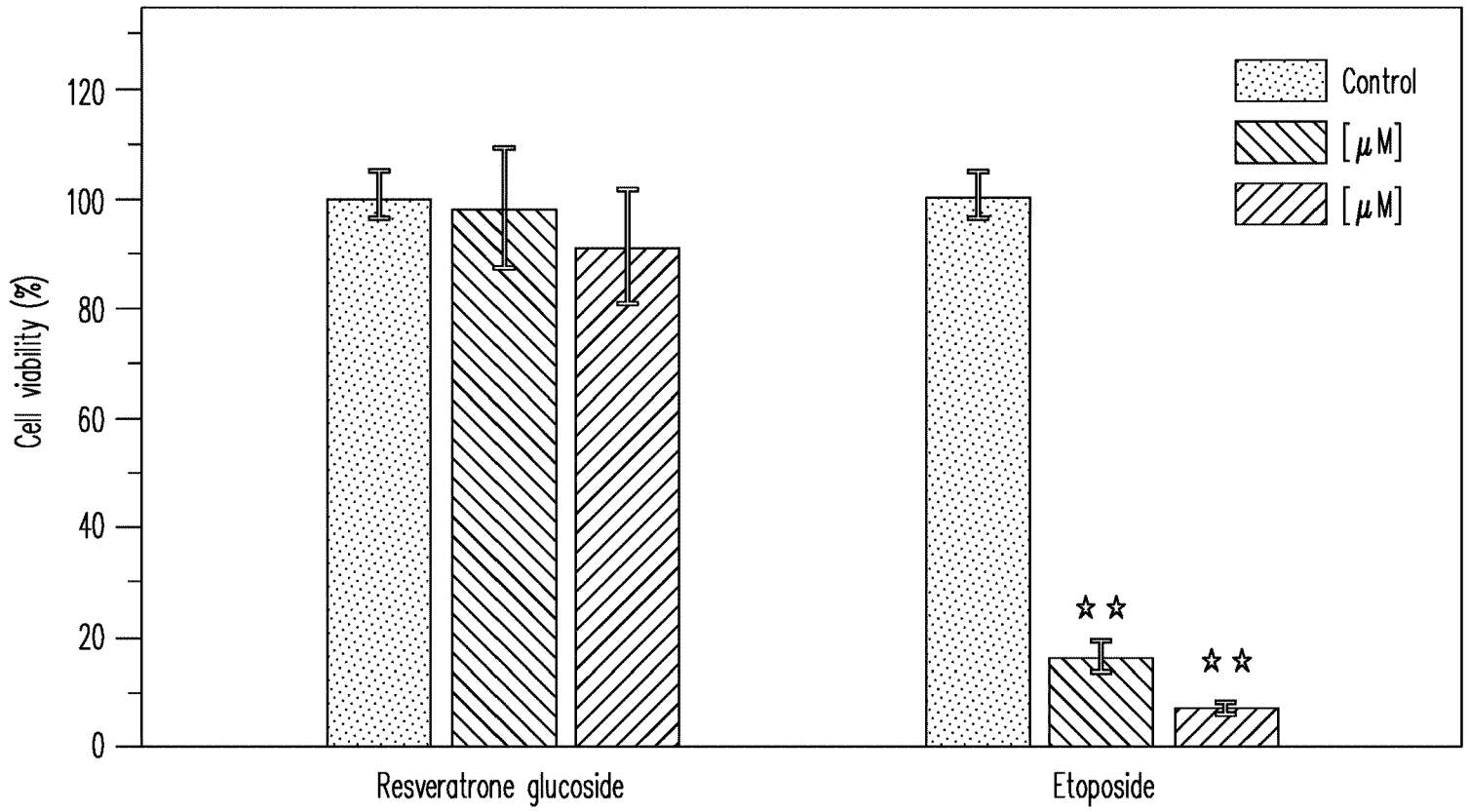
FIG. 14 is a graph showing the result of Blue Exclusion Test for a blank test (Control), a fluorescent compound of the present invention (Resveratrone glycoside) and a comparative compound (Etoposide).

FIG. 14 is a graph showing the result of Blue Exclusion Test for the control group (blank), the test compound (Resveratrone glucoside) and the comparative compound (etoposide), respectively. In FIG. 14, the test compound (left side) results to a number of cells similar to that of the control group in both test concentrations (1 μM and 10 μM), while the comparative compound (right side) results to a remarkably reduced number of cells in both test concentrations (1 μM and 10 μM).

Therefore, it can be understood from FIG. 14 that the test compound (Resveratrone glucoside) of the present invention has no or little cell toxicity and a very high stability in comparison with the commercial anticancer agent (Etoposide).

Test Example 3

Western Blotting Test

A breast epithelial cell line is cultured in a blank test (control group) and in the presence of a test compound (Resveratrone glucoside), respectively, and an osteosarcoma cell line (U2OS) is cultured in the presence of a comparative compound (Etoposide).

Figure 15:
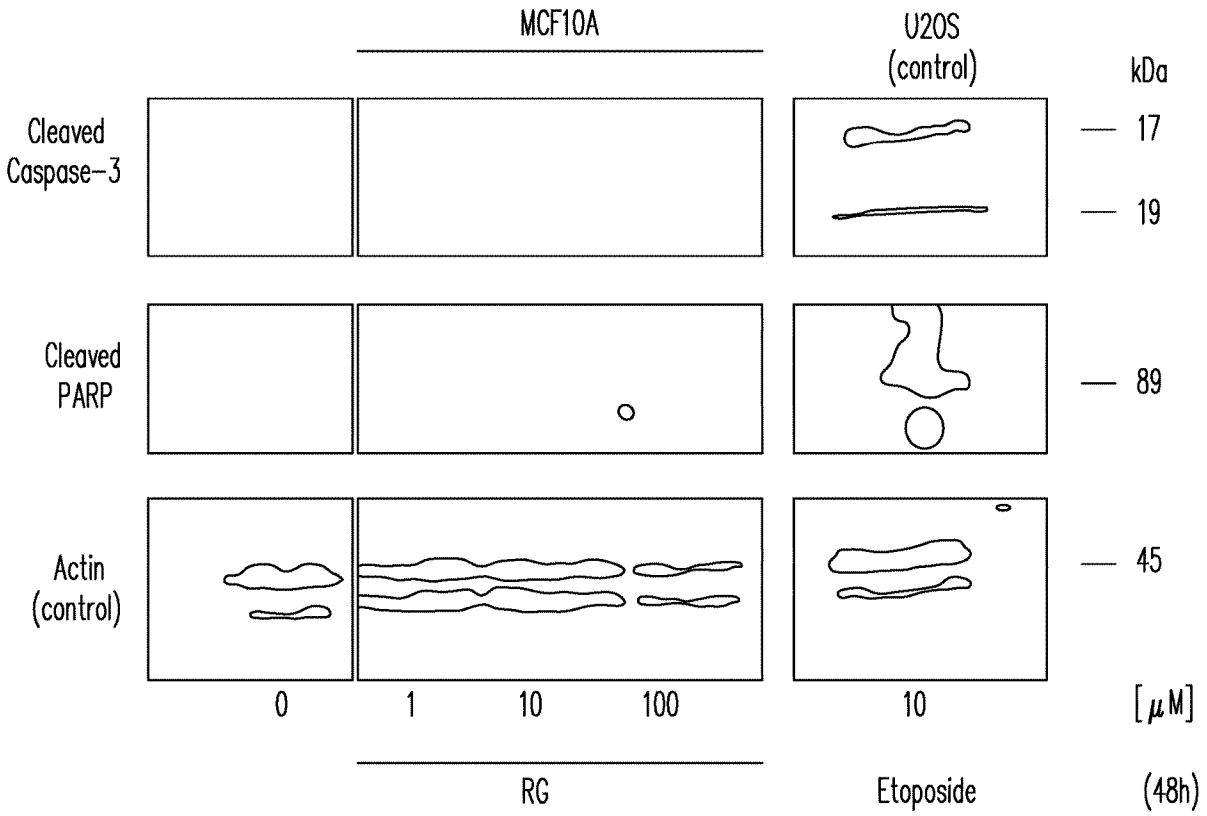
FIG. 15 is a graph showing the result of Western Blotting Test for a blank test (Control), a fluorescent compound of the present invention (Resveratrone glycoside) and a comparative compound (Etoposide).

After a certain period of time, the degree of cell extinction is evaluated by examining the degree of expression of extinction and damage of a specific factor by using Western Blotting Test and the result is shown in FIG. 15.

In FIG. 15, the blank test (left side, Control group, concentration of 0 μM) and the test compound (center side, Resveratrone glucoside, three concentrations of 1, 10 and 100 μM) show only a peak at 45 kDa position and no peak at 17 kDa, 19 kDa and 89 kDa positions which result from cell extinction and damage. Therefore, it can be understood that the test compound does not give any significant level of cell extinction and damage.

Further, the comparative compound (right side. Etoposide, concentration of 10 μM) shows a significantly remarkable peak at 17 kDa, 19 kDa and 89 kDa positions which result from cell extinction and damage, by which it can be understood that a lot of cells are extinguished and/or damaged.

As a result, it can be understood from FIG. 14 that the test compound (Resveratrone glucoside) of the present invention has no or little cell toxicity.

The terms used in FIG. 14 have the following meanings:

Caspase-3: one of proteins found when cells die

PARP: one of proteins found when cells die

Actin: a procedure for confirming whether the current Western Blotting System is normally operating (control group)

Osteosarcoma cells (U2OS): one of cancer cell lines

Etoposide: one of commercial anticancer agents

In the result using osteosarcoma cells (U2OS) in the presence of a comparative compound (etoposide), the expression of the above specific proteins means that the Western Blotting System is normally operating.

INDUSTRIAL APPLICABILITY

The new water-soluble fluorescent compound of the present invention can be usefully utilized in the field of organic fluorescent element, display element, spectrometer, two-photon absorptive storing device, laser micro processing apparatus, photo dynamic therapy apparatus and the like.

What is claimed is:

1. A display element comprising a fluorescent compound represented by the following Formula 1:

[Formula 1]

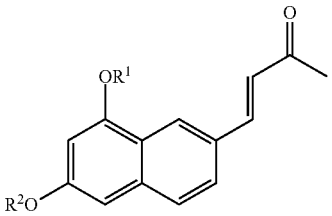

wherein, $R^1$ and $R^2$ are independently selected from the group consisting of a hydrogen atom; straight-chain or branched C1-C10 alkyl; C1-C10 alkylcarbonyl; C3-C6 cycloalkyl; C6-C30 aryl; and C5-C30 heteroaryl comprising:

at least one heteroatom N, O or S;

a residue of a water-soluble natural compound;

a residue of a water-soluble polymer; or a residue of a water-soluble high molecular organic compound, provided that at least one of $R^1$ and $R^2$ represents a residue of a water-soluble natural compound, a residue of a water-soluble polymer or a residue of a water-soluble high molecular organic compound, said water-soluble natural compound, water-soluble polymer or water-soluble high molecular organic compound selected from a group consisting of monosaccharide, disaccharide, oligosaccharide, a water-soluble vitamin, polyethylene glycol, polypropylene glycol, PVA, crospovidone, PVP, and PVP-PVA.

2. A spectrometer, a two-photon absorptive storing device, a laser micro processing apparatus, or a photo dynamic therapy apparatus, comprising a fluorescent compound represented by the following Formula 1:

[Formula 1]

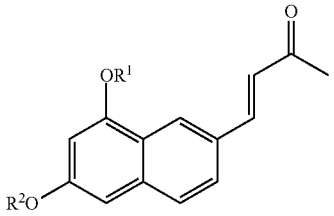

wherein, $R^1$ and $R^2$ are independently selected from the group consisting of a hydrogen atom; straight-chain or branched C1-C10 alkyl; C1-C10 alkylcarbonyl; C3-C6 cycloalkyl; C6-C30 aryl; and C5-C30 heteroaryl comprising:

at least one heteroatom N, O or S;

a residue of a water-soluble natural compound;

a residue of a water-soluble polymer; or a residue of a water-soluble high molecular organic compound, provided that at least one of $R^1$ and $R^2$ represents a residue of a water-soluble natural compound, a residue of a water-soluble polymer or a residue of a water-soluble high molecular organic compound, said water-soluble natural compound, water-soluble polymer or water-soluble high molecular organic compound selected from a group consisting of monosaccharide, disaccharide, oligosaccharide, a water-soluble vitamin, polyethylene glycol, polypropylene glycol, PVA, crospovidone, PVP, and PVP-PVA.

*3. A fluorescent compound comprising a compound represented by the following Formula 1:*

[Formula 1]

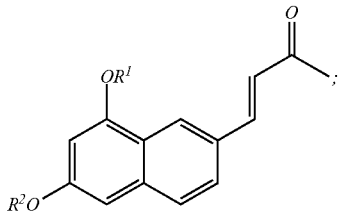

wherein $R^1$ is selected from the group consisting of a hydrogen atom; straight-chain or branched C1-C10 alkyl; C1-C10 alkylcarbonyl; C3-C6 cycloalkyl; C6-C30 aryl; and C5-C30 heteroaryl including at least one heteroatom N, O or S;

wherein $R^2$ is a residue of a water-soluble natural compound or a residue of a water-soluble high molecular organic compound;

wherein said residue of a water-soluble natural compound is a substituent selected from the group consisting of a monosaccharide, and a disaccharide or oligomer thereof; and wherein said residue of a water-soluble high molecular organic compound is a substituent selected from the group consisting of polyethylene glycol, polypropylene glycol, polyvinyl alcohol, crospovidone, polyvinylpyrrolidone, and PVP-PVA.

4. The fluorescent compound according to claim 3, wherein the fluorescent compound includes the fluorescent compound represented by the following Formula 2:

[Formula 2]

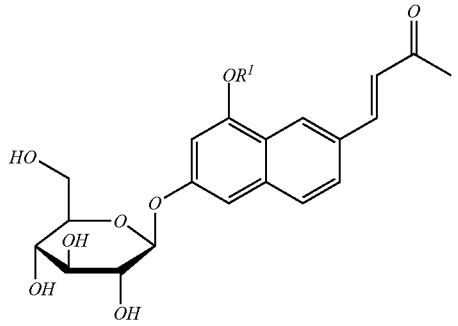

wherein $R^1$ is selected from the group consisting of a hydrogen atom; straight-chain or branched C1-C10 alkyl; C1-C10 alkylcarbonyl; C3-C6 cycloalkyl; C6-C30 aryl; and C5-C30 heteroaryl including at least one heteroatom N, O or S.

5. The fluorescent compound according to claim 3, wherein the fluorescent compound includes the fluorescent compound represented by Formula 6:

[Formula 6]

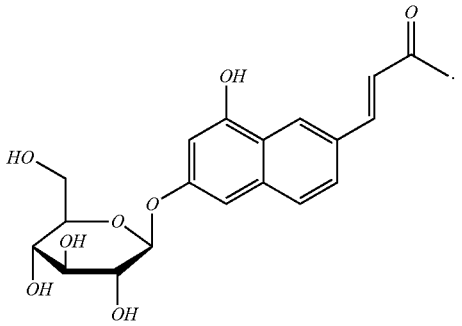

6. A fluorescent compound comprising a compound represented by the following Formula 9, or Formula 12:

[Formula 9]

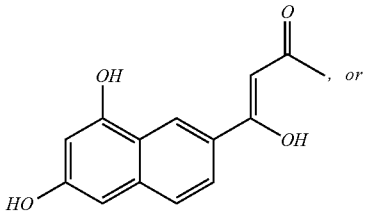

[Formula 12]

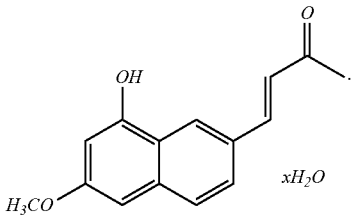

7. A fluorescent compound comprising a compound represented by the following Formula 13:

[Formula 13]

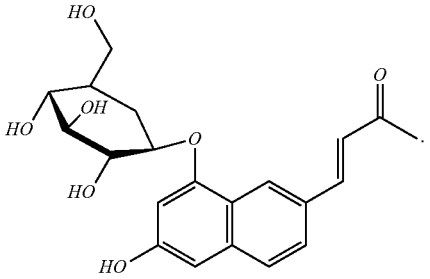

* * * * *